(12) United States Patent
Fischer et al.

(10) Patent No.: US 8,637,425 B2
(45) Date of Patent: Jan. 28, 2014

(54) PROCESS FOR PREPARING A NI/SN SUPPORTED CATALYST FOR THE SELECTIVE HYDROGENATION OF POLYUNSATURATED HYDROCARBONS

(75) Inventors: Lars Fischer, Vienne (FR); Anne-Claire Dubreuil, Lyons (FR); Cecile Thomazeau, Lyons (FR); Layane Deghedi, Lyons (FR); Jean-Pierre Candy, Caluire (FR); Jean-Marie Basset, Caluire et Cuire (FR); Fabienne Le Peltier, Rueil Malmaison (FR)

(73) Assignee: IFP Energies nouvelles, Rueil-Malmaison Cedex (FR)

( * ) Notice: Subject to any disclaimer, the term of this patent is extended or adjusted under 35 U.S.C. 154(b) by 329 days.

(21) Appl. No.: 12/857,029

(22) Filed: Aug. 16, 2010

(65) Prior Publication Data

US 2011/0166398 A1  Jul. 7, 2011

(30) Foreign Application Priority Data

Aug. 17, 2009  (FR) ...................................... 09 03988

(51) Int. Cl.
*B01J 21/00*  (2006.01)
(52) U.S. Cl.
USPC ........... 502/242; 502/335; 502/337; 585/263; 585/266; 585/250
(58) Field of Classification Search
USPC ........................ 502/337, 242; 585/266, 263
See application file for complete search history.

(56) References Cited

U.S. PATENT DOCUMENTS

| | | | |
|---|---|---|---|
| 3,480,531 A * | 11/1969 | Mulaskey | ...................... 208/143 |
| 4,504,593 A | 3/1985 | Trinh Dinh et al. | |
| 4,548,918 A * | 10/1985 | Bournonville et al. | ....... 502/154 |
| 5,475,174 A | 12/1995 | Lucas et al. | |
| 6,566,573 B1 | 5/2003 | Bharadwaj et al. | |

FOREIGN PATENT DOCUMENTS

| | | |
|---|---|---|
| FR | 2539647 A1 | 7/1984 |
| FR | 2698351 A1 | 5/1994 |
| FR | 2792645 A1 | 10/2000 |

OTHER PUBLICATIONS

Institut National De La Propriete Industrielle. "Search Report and Written Opinion." FR 0903988. Appplicant: IFP. Mailed Mar. 12, 2010.

* cited by examiner

*Primary Examiner* — Colleen Dunn
*Assistant Examiner* — Haytham Soliman
(74) *Attorney, Agent, or Firm* — Millen, White, Zelano & Branigan, P.C.

(57) ABSTRACT

A process is described for preparing a catalyst comprising at least one porous support and at least one metallic phase containing nickel and tin in a proportion such that the Sn/Ni molar ratio is in the range 0.01 to 0.2, said process comprising at least the following steps in succession:
  a) depositing nickel on at least said support in order to obtain a supported nickel-based monometallic catalyst;
  b) reducing said monometallic catalyst in the presence of at least one reducing gas;
  c) depositing, in the gas phase and in the presence of at least one reducing gas, at least one organometallic tin compound onto said reduced monometallic catalyst; and
  d) activating the solid derived from said step c) in the presence of at least one reducing gas.

10 Claims, No Drawings

PROCESS FOR PREPARING A NI/SN SUPPORTED CATALYST FOR THE SELECTIVE HYDROGENATION OF POLYUNSATURATED HYDROCARBONS

This application is related to concurrently filed application Ser. No. 12/856,932 "PROCESS FOR PREPARING A SUPPORTED CATALYST BASED ON Ni AND A METAL FROM GROUP IB, FOR THE SELECTIVE HYDROGENATION OF POLYUNSATURATED HYDROCARBONS" by Lars Fischer, et al., claiming priority of FR 09/03.987, filed Aug. 17, 2009, incorporated by reference herein.

FIELD OF THE INVENTION

The present invention relates to the selective hydrogenation of polyunsaturated compounds present in, a hydrocarbon feed such as, for example, in steam cracked gasolines. These gasolines contain gum-generating compounds, in particular diolefins and alkenylaromatics, in particular mixed with mono-olefinic and aromatic compounds. In order to be able to upgrade steam cracked gasolines, they must be freed of their diolefins or respectively alkenylaromatic compounds; the diolefins are selectively hydrogenated to mono-olefins and the alkenylaromatics are selectively hydrogenated to aromatics. More precisely, the invention relates to a process for preparing a supported catalyst containing tin and nickel for the selective hydrogenation of polyunsaturated compounds present in hydrocarbon cuts.

PRIOR ART

Selective hydrogenation treatments are generally carried out on metallic catalysts deposited onto an amorphous or crystalline support. The metals used are metals from group VIII and of these, nickel can be pointed out as being in routine use.

However, nickel catalysts are not sufficiently selective as they have a marked tendency to hydrogenate a large part of the mono-olefins contained in the feed, even when the hydrogenations are carried out at low pressure, of the order of 30 to 50 bar, and at low temperature, in the range 50° C. to 180° C. (degrees Celsius).

It is known that improving the selectivity of those catalysts can be achieved by injecting sulphur-containing compounds before bringing the catalyst into contact with the reactive feed in order to obtain a catalyst passivated with sulphur. These compounds may be selected from the following compounds: thiophene, thiophane, alkylmonosulphides such as dimethyl sulphide, diethylsulphide, dipropylsulphide or propylmethylsulphide. Such sulphurization is, however, difficult to carry out as it is necessary for the sulphurized compound to be distributed very evenly throughout the catalytic bed in order to achieve a marked effect on selectivity. Furthermore, that procedure is expensive and lengthy, which results in a loss of production.

The intrinsic lack of selectivity of a nickel catalyst is not only manifested as regards mono-olefins, but also as regards aromatics. If the surface of the Ni particles were surface passivated by sulphur-containing organic compounds in a highly controlled manner, a priori onto clearly distinct Ni sites, and in an amount of one atom of S per approximately 4 or 5 surface Ni atoms [T E Fischer, S R Kelemen, J Catal 53, 24 (1978) or GB1565754], hydrogenation of the aromatic rings would be dispensed with and hydrogenation of the mono-olefinic compounds would be greatly slowed. Controlling the deposition of sulphur so closely on an industrial scale as well as controlling the stability of that system under the reaction conditions used for selective hydrogenations (25-30 bar, 50-180° C.) is difficult to achieve, however. Thus, when starting up with a nickel catalyst, even when passivated by a sulphur-containing compound of the type indicated above, it is necessary to use a non-reactive start-up feed, containing neither dielefins nor mono-olefins and very few aromatics. The hydrogenation of the diolefins or possibly the mono-olefins on fresh catalysts which are highly active causes enough heat to be released to raise the temperature of the catalyst to levels well beyond 200° C., which may cause hydrogenation of the aromatics. This latter reaction is even more exothermic and the temperature may exceed 600° C., which results in causing cracking of the hydrocarbons, a reaction which itself is also highly exothermic. In this manner, the temperatures reached during these runaways may exceed the nominal temperatures for steel reactors, meaning replacement not only of the catalyst charge but also of the reactor itself.

Another method for improving catalytic selectivity consists of pre-passivating the Ni catalyst in the oxidized state and in the absence of hydrogen, by impregnation with an organic sulphur compound, for example 2,2-dithio-bis-ethanol (DEODS), as described in patent EP-0 466 567. The polysulphide decomposes in hydrogen in the hydrogenation reactor, simultaneously with the reduction of nickel, and a reactive feed may subsequently be introduced with no danger of reaction runaway. However, given that reduction and passivation with sulphur take place at the same, time, it is even more difficult under these conditions to obtain homogeneous passivation of the Ni surface with the desired stoichiometry and only at the desired Ni sites. In order to avoid the presence of non-passivated reduced Ni particles, the polysulphide is introduced in excess and over-passivation with the partial formation of the phase $Ni_3S_2$ cannot in general be avoided, which significantly reduces the catalytic activity even as regards diolefins (B W Hoffer, R L C Bonne, A D van Langeveld, C Griffiths, C M Lok, I A Moulijn, Fuel 83 (2004), 1-8).

It is also known that bimetallic catalysts may produce gains in selectivity and stability. For selective hydrogenation catalysts, it is known that associations of palladium with a second metal render the catalysts more selective but less active. Such associations have only been proposed for the selective hydrogenation of cuts containing hydrocarbons containing between 2 and 4 carbon atoms, in which usually a first reactor operates with a monometallic palladium catalyst to carry out the major portion of the conversion, and a second reactor containing a bimetallic catalyst completes the conversion in a more selective manner. As an example, U.S. Pat. No. 5,356,851 discloses that it is advantageous to associate a metal from group VIII (preferably palladium) with an element such as indium or gallium for applications for the selective hydrogenation of polyunsaturated compounds. Similarly, Pd—Cu (U.S. Pat. No. 5,464,802), Pd—Ag (U.S. Pat. No. 4, 547,600), Pd—Sn and Pd—Pb (JP-59227829) associations or a combination of palladium and an alkali metal (EP-0 722 776) have been identified for their hydrogenation performances. All of these patents are aimed at improving the mono-olefins yield.

Bimetallic nickel-based catalysts are also described in the prior art. Patent GB 1 565 754 describes the introduction of 10 ppm of an element from the platinum group, such as ruthenium, rhodium, palladium, osmium, iridium or platinum, and preferably palladium, into a catalyst for the selective hydrogenation of C3, C4 cuts or gasoline containing 10% of Ni supported on sepiolite. This introduction has the effect of increasing the reducibility of Ni after regeneration, but the subsequent introduction of sulphide compounds is still necessary for passivation. U.S. Pat. No. 5,997,835 describes the introduction of gold into a supported nickel catalyst by an aqueous phase method for methane steam reforming; the effect of introducing the gold is to slow down catalyst deactivation.

Patent FR-2 792 645 describes the preparation, in an aqueous phase at a pH of less than 10, of a bimetallic catalyst associating a metal from group VIII (preferably platinum, palladium and nickel) and a metal preferably selected from germanium, tin, silver and gold. Patent FR-2 539 647 describes the introduction of germanium, tin or lead in the form of a solution of an alkyl of that metal, and of a metal from group VIII (preferably platinum, palladium, nickel and cobalt). Those catalysts are of interest in applications for the selective hydrogenation of polyunsaturated compounds, with the aim of increasing the yield of mono-olefins, or for hydrodesulphurization applications.

Patent FR-2 698 351 discloses that it is advantageous to associate a metal from group VIII selected from iridium, osmium, nickel, palladium, platinum and rhodium (rhodium being the preferred metal) and an additional metal selected from group IVa constituted by tin, germanium and lead for the selective hydrogenation of 4-vinyl-cyclohexene to vinyl-cyclohexane. The preferred preparation method consists of preparing a monometallic catalyst based on a metal from group VIII, to reduce it then to impregnate it, either in aqueous solution or in organic solution or in the gas phase, with a compound of a metal from group IVa. The product obtained may optionally be reduced before use. The percentages of the metals employed are preferably in the range 1% by weight to 3% by weight for the metals from group VIII and in the range 0.01% by weight to 15% by weight for the additional metal, which corresponds to a molar ratio of the group VIII element to the group IVa element in the range 0.3 to 3.

The aim of the present invention is to provide a catalyst containing a metallic phase based on nickel and tin, prepared by a novel preparation process, for the selective hydrogenation of polyunsaturated compounds present in a hydrocarbon cut. More precisely, it proposes providing an alternative catalyst to the nickel-based catalysts passivated with sulphur which are known in the prior art.

SUMMARY AND ADVANTAGE OF THE INVENTION

The present invention provides a process for preparing a catalyst comprising at least one porous support and at least one metallic phase containing nickel and tin in a proportion such that the Sn/Ni molar ratio is in the range 0.01 to 0.2, said process comprising at least the following steps in succession:
  a) depositing nickel on at least said support in order to obtain a supported nickel-based monometallic catalyst;
  b) reducing said monometallic catalyst in the presence of at least one reducing gas;
  c) depositing, in the gas phase and in the presence of at least one reducing gas, at least one organometallic tin compound onto said reduced monometallic catalyst; and
  d) activating the solid derived from said step c) in the presence of at least one reducing gas in order to obtain a supported catalyst having a metallic phase based on nickel and tin in which the tin represents 0.02% to 15% by weight of the mass of said catalyst and the nickel represents 1% to 50% by weight of the mass of the catalyst.

The present invention also pertains to a process for the selective hydrogenation of a feed of polyunsaturated hydrocarbons, said process comprising passing said feed into at least one reaction unit provided with at least one supported catalyst comprising at least one metallic phase containing tin and nickel prepared in accordance with the preparation process of the invention.

The catalyst prepared using the process of the invention and used in a process for the selective hydrogenation of polyunsaturated hydrocarbons produces improved catalytic performances in terms of selectivity for mono-unsaturated compounds. Furthermore, the catalyst prepared using the process of the invention and employed in a process for the selective hydrogenation of polyunsaturated hydrocarbons substantially limits or even eliminates the hydrogenation of aromatic rings present in polyunsaturated compounds, such as aromatic, styrene or indene compounds, which means that runaway of the reactions can be avoided and means that the compounds with an aromatic ring issuing from said selective hydrogenation process of the invention, can be upgraded in a variety of applications.

DESCRIPTION OF THE INVENTION

The present invention concerns a process for preparing a catalyst comprising at least one porous support and at least one metallic phase containing nickel and tin in a proportion such that the Sn/Ni molar ratio is in the range 0.01 to 0.2, said process comprising at least the following steps in succession:
  a) depositing nickel on at least said support in order to obtain a supported nickel-based monometallic catalyst;
  b) reducing said monometallic catalyst in the presence of at least one reducing gas;
  c) depositing, in the gas phase and in the presence of at least one reducing gas, at least one organometallic tin compound onto said reduced monometallic catalyst; and
  d) activating the solid derived from said step c) in the presence of at least one reducing gas in order to obtain a supported catalyst having a metallic phase based on nickel and tin in which the tin represents 0.02% to 15% by weight of the mass of said catalyst and the nickel represents 1% to 50% by weight of the mass of said catalyst.

In accordance with the preparation process of the invention, it is essential that said steps a), b), c) and d) are carried out in succession one after the other. However, intermediate steps may be carried out between each of said steps a), b), c) and d) as long as the order of carrying out steps a) to d) is maintained.

In accordance with the invention, the catalyst prepared using the process of the invention contains nickel and tin deposited on a porous support. The nickel content is generally in the range 1% by weight to 50% by weight, preferably in the range 5% by weight to 40% by weight and more preferably in the range 8% by weight to 30% by weight with respect to the catalyst mass. The tin content is generally in the range 0.02% by weight to 15% by weight of the catalyst mass. The molar ratio Sri/Ni is generally in the range 0.01 to 0.2, preferably in the range 0.025 to 0.055, and more preferably in the range 0.03 to 0.05.

The porous support present in the catalyst prepared using the process of the invention generally comprises at least one refractory oxide which is generally selected from oxides of metals from groups 2, 3, 4, 13 and 14 of the new periodic table of the elements such as, for example, oxides of magnesium, aluminium, silicon, titanium, zirconium or thorium, alone or as a mixture or mixed with other oxides of metals from the periodic table of the elements. Coal may also be used. The preferred support is selected from aluminas, silicas and silicas-aluminas, and more preferably it is an alumina or a silica. The pore volume of the support is generally in the range 0.1 $cm^3/g$ to 1.5 $cm^3/g$, preferably in the range 0.5 $cm^3/g$ to 1 $cm^3/g$. The specific surface area of the support is generally in the range 10 $m^2/g$ to 250 $m^2/g$, preferably in the range 30 $m^2/g$ to 200 $m^2/g$ and more preferably in the range 40 $m^2/g$ to 180 $m^2/g$. Said porous support is advantageously in the form of beads, extrudates, pellets or irregular and non-spherical agglomerates the specific shape of which may result from a crushing step. Highly advantageously, said support is in the form of beads or extrudates.

In accordance with step a) of the preparation process of the invention, nickel is deposited on the porous support. The nickel can be deposited onto said support using any method which is known to the skilled person. As an example, the deposit is produced by impregnation, consisting of bringing said porous support into contact with at least one aqueous or organic solution of at least one nickel compound or with a suspension of at least one organic or inorganic nickel compound, or deposition may be accomplished using deposition-precipitation methods which are well known to the skilled person [J W Geus, Preparation of Catalysts III, in G Poncelet, P Grange, P A Jacobs (Eds), Elsevier, Amsterdam 1983, 1]. Deposition of the nickel onto the support is optionally followed by one or more washes and/or optionally by evaporating off the solvent. Advantageously, deposition of the nickel onto the porous support is followed by one or more heat or chemical treatments resulting in a monometallic supported catalyst based on nickel mainly in the oxide state or mainly in the metallic state. Said step a) results in the preparation of a supported nickel-based monometallic catalyst.

In accordance with step b) of the process of the invention, at least one step for reduction of said monometallic catalyst derived from step a) is carried out in the presence of a reducing gas, preferably hydrogen. Said step b) is carried out at a temperature in the range 100° C. to 600° C., preferably in the range 200° C. to 500° C., for a period in the range 1 hour to 40 hours, preferably in the range 5 hours to 30 hours. The ramp-up to this reduction temperature is generally slow, for example fixed at between 0.1° C./minute and 5° C./minute. These conditions means that a very substantially reduced supported monometallic catalyst can be obtained.

In accordance with step c) of the process of the invention, at least one step is carried out, in the gas phase and in the presence of at least one reducing gas, for depositing at least one organometallic tin compound onto said reduced monometallic catalyst. The reducing gas is preferably hydrogen. Said step c) is carried out at a temperature in the range 10° C. to 100° C., preferably in the range 20° C. to 50° C., and for a period in the range 50 minutes to 5 hours. Step c) is carried out in the absence of solvent.

The organometallic tin compound used to carry out said step c) is generally selected from the group constituted by alkyltin and aryltin compounds. Hence, said organometallic tin compound preferably has formula $Sn(R)_nH_{4-n}$ were R is an alkyl radical or an aryl radical containing 1 to 12 carbon atoms, and n is a whole number in the range 1 to 4, preferably in the range 2 to 4 and highly preferably n=2 or n=4; radicals R may be identical or different. Preferably, said organometallic tin compound is selected from the group constituted by tetrabutyltin, tetramethyltin, tetraethyltin, tetrapropyltin, diphenyltin, tributyltin hydride and tributyltin chloride. More preferably, said organometallic tin compound is tetrabutyltin.

In accordance with step d) of the process of the invention, at least one step for activation of said solid derived from said step c) is carried out in the presence of at least one reducing gas, preferably hydrogen. Said activation step d) is carried out at a temperature in the range 100° C. to 550° C., preferably in the range 150° C. to 500° C., more preferably in the range 330° C. to 500° C., for a period in the range 1 hour to 40 hours, preferably in the range 3 hours to 20 hours. The ramp-up to this activation temperature is generally slow, for example fixed at between 0.1° C./minute and 5° C./minute.

The catalyst obtained at the end of the preparation process of the invention is advantageously used directly at the end of said step d) in a reaction unit carrying out the conversion of a hydrocarbon feed, in particular in a reaction unit carrying out selective hydrogenation of a polyunsaturated hydrocarbon feed. Said catalyst prepared using the process of the invention may also be stored in air then reduced prior to use. The reduction then generally consists of a slow temperature ramp-up, for example in the range 0.1° C./minute to 5° C./minute, in a stream of reducing gas, preferably in hydrogen, to the maximum reduction temperature, in the range 100° C. to 600° C., preferably in the range 200° C. to 500° C., followed by maintaining that temperature for a period in the range 1 hour to 40 hours, preferably in the range 5 hours to 30 hours.

The present invention also pertains to a process for the selective hydrogenation of a polyunsaturated hydrocarbon feed, said process comprising passing said feed into at least one reaction unit provided with at least one supported catalyst comprising at least one metallic phase containing tin and nickel prepared in accordance with the preparation process of the invention.

Said polyunsaturated hydrocarbon feed treated in the selective hydrogenation process of the invention is advantageously a steam cracked gasoline comprising polyunsaturated hydrocarbons containing at least 4 carbon atoms and having an end point of up to 220° C. More precisely, said polyunsaturated hydrocarbons present in the feed treated using the selective hydrogenation process of the invention are in particular diolefin compounds, styrene compounds and indene compounds. Regarding the diolefin compounds, said feed in particular contains butadiene, isoprene and cyclopentadiene. Regarding the styrene compounds, said feed in particular contains styrene and alpha-methyl styrene. Regarding the indene compounds, said feed in particular contains indene.

The selective hydrogenation process of the invention is intended to selectively hydrogenate said polyunsaturated hydrocarbons present in said feed to be treated in a manner such that the diolefin compounds are partially hydrogenated into mono-olefins and such that the styrene and indene compounds are partially hydrogenated into the corresponding aromatic compounds.

The effluent obtained after carrying out the selective hydrogenation process of the invention has a substantially reduced polyunsaturated hydrocarbons content; in particular, it has a reduced diolefin compounds, styrene compounds and indene compounds content, while retaining a quantity of aromatic compounds (more precisely a quantity of aromatic rings) close to that present in said polyunsaturated hydrocarbon feed. Said effluent is advantageously upgradeable as a base in a gasoline or can be used as a base for upgrading aromatic compounds.

The selective hydrogenation process of the invention is advantageously carried out under pressure, in the liquid phase, in the presence of a quantity of hydrogen that is in slight excess with respect to the stoichiometric value allowing the selective hydrogenation of the polyunsaturated compounds present in the hydrocarbon feed, i.e. an excess which is generally in the range 5% to 30%. The selective hydrogenation process of the invention is carried out at a temperature in the range 20° C. to 200° C. The pressure is generally sufficient to maintain at least 80% by weight of the feed to be treated in the liquid phase at the inlet to the reaction unit. It is generally in the range 0.4 MPa to 5 MPa, more advantageously in the range 1 MPa to 4 MPa. The hourly space velocity (defined as the ratio of the volume flow rate of feed to the volume of catalyst) established under these conditions is generally in the range $0.2\ h^{-1}$ to $30\ h^{-1}$, and preferably in the range $1\ h^{-1}$ to $20\ h^{-1}$, more preferably in the range $2\ h^{-1}$ to $10\ h^{-1}$.

The selective hydrogenation process is technically undertaken, for example, by injection, as an upflow or downflow, of the feed and hydrogen into a fixed bed reactor. It may also advantageously be carried out by implanting at least said supported catalyst containing tin and nickel in a reactive distillation column or in reactor-exchangers.

The following examples illustrate the invention without limiting its scope.

EXAMPLE 1 (In Accordance with the Invention)

Preparation of a Catalyst B Supported on Alumina and Containing Nickel and Tin

A commercial Ni/alumina type catalyst (LD 241, Axens, denoted catalyst A) was used to prepare a catalyst based on nickel and tin in accordance with the invention (catalyst B). Said commercial catalyst had a nickel content of 10% by weight, a specific surface area of $70\ m^2/g$, a total pore volume of $0.63\ cm^3/g$ and a bead diameter in the range 2 to 4 mm.

The protocol for preparing catalyst B was as follows. A quantity of 0.5 g of monometallic catalyst A was pre-reduced in a stream of hydrogen at 400° C. for 14 hours. Tin was deposited onto said catalyst A in the gas phase: 9 mg of tetrabutyltin (Aldrich) was injected onto the pre-reduced catalyst A at ambient temperature and in an atmosphere of hydrogen. After 3 hours of contact, the temperature was raised to 450° C. in a stream of hydrogen, at a rate of 2° C./minute. The temperature was then maintained at 450° C. for 4 hours. Finally, the catalyst was cooled and stored in air.

Catalyst B obtained thereby contained 9.9% by weight of Ni and 0.6% by weight of tin (according to elemental analysis), corresponding to a Sn/Ni molar ratio of 0.030.

EXAMPLE 2 (Comparative)

Preparation of a Catalyst C Supported on Alumina and Containing Nickel and Tin, the Tin Being Deposited in the Liquid Phase A catalyst based on nickel and tin (catalyst C) was prepared from catalyst A using the following protocol. A quantity of 1 g of monometallic catalyst A was pre-reduced in a stream of hydrogen at 400° C. for 14 hours. Catalyst C was prepared by bringing 1 g of monometallic catalyst A in the reduced state into contact with 20 mL of a solution of tetrabutyltin (Aldrich) in heptane (Acros) (concentration $4.5 \times 10^{-4}$ mol/L) for 10 hours at ambient temperature in a hydrogen atmosphere and with stirring. The solid obtained was then recovered by filtration, washed with heptane then introduced directly into the autoclave for the styrene hydrogenation test.

Catalyst C obtained thereby contained 9.9% by weight of Ni and 0.6% by weight of tin (according to elemental analysis), corresponding to a Sn/Ni molar ratio of 0.030.

EXAMPLE 3 (Comparative)

Preparation of a Monometallic Catalyst D Supported on Silica Containing Nickel

A Ni/silica (catalyst D) type catalyst was prepared by cation exchange of the $[Ni(NH_3)_6]^{2+}$ salt on silica. The impregnation solution was prepared by mixing a solution of nickel nitrate (Aldrich) with concentration $7 \times 10^{-3}$ mol/L with an ammoniacal solution (Aldrich) at a concentration of 0.4 mol/L. A quantity of 4 g of silica (Aerosil-200, Degussa) was brought into contact with 50 mL of the impregnation solution for 24 hours, at ambient temperature and with stirring. The solid was then recovered by filtering, washed with permutated water, dried in a vacuum oven at 80° C. then 100° C. and finally treated in a stream of hydrogen at 500° C. before being cooled and stored in air.

The monometallic catalyst D obtained thereby contained 11.7% by weight of Ni (according to elemental analysis).

EXAMPLE 4 (In Accordance with the Invention)

Preparation of a Catalyst E Supported on Silica and Containing Nickel and Tin

A catalyst based on nickel and tin in accordance with the invention (catalyst E) was prepared from catalyst D using the following protocol. A quantity of 0.41 g of monometallic catalyst D was pre-reduced in a stream of hydrogen at 400° C. for 14 hours. The tin was deposited in the gas phase: 10 mg of tetrabutyltin (Aldrich) was injected at ambient temperature and in an atmosphere of hydrogen onto the pre-reduced catalyst D. After 3 hours of contact, the temperature was raised to 350° C. in a stream of hydrogen at a rate of 2° C./minute. The temperature was then maintained at 350° C. for 4 hours. Finally, the catalyst was cooled and stored in air.

Catalyst E obtained thereby contained 11.6% by weight of Ni and 0.8% by weight of tin (according to elemental analysis), corresponding to a Sn/Ni molar ratio of 0.034.

EXAMPLE 5 (In Accordance with the Invention)

Preparation of a Catalyst F Supported on Silica and Containing Nickel and Tin

Another catalyst based on nickel and tin in accordance with the invention (catalyst F) was prepared from catalyst D using the following protocol. A quantity of 0.41 g of monometallic catalyst D was pre-reduced in a stream of hydrogen at 400° C. for 14 hours. The tin was deposited in the gas phase: 10 mg of tetrabutyltin (Aldrich) was injected at ambient temperature and in an atmosphere of hydrogen onto the pre-reduced catalyst D. After 3 hours of contact, the temperature was raised to 450° C. in a stream of hydrogen at a rate of 2° C./minute. The temperature was then maintained at 450° C. for 4 hours. Finally, the catalyst was cooled and stored in air.

Catalyst F obtained thereby contained 11.6% by weight of Ni and 0.8% by weight of tin (according to elemental analysis), corresponding to a Sn/Ni molar ratio of 0.034.

EXAMPLE 6 (Comparative)

Preparation of a Catalyst G Supported on Silica and Containing Nickel and Tin Such that the Sn/Ni Molar Ratio=0.25

Another catalyst based on nickel and tin (catalyst G) was prepared from catalyst D using the following protocol. A quantity of 0.41 g of monometallic catalyst D was pre-reduced in a stream of hydrogen at 400° C. for 14 hours. The tin was deposited in the gas phase: 71 mg of tetrabutyltin (Aldrich) was injected at ambient temperature and in an atmosphere of hydrogen onto the pre-reduced catalyst D. After 3 hours of contact, the temperature was raised to 450° C. in a stream of hydrogen at a rate of 2° C./minute. The temperature was then maintained at 450° C. for 4 hours. Finally, the catalyst was cooled and stored in air.

Catalyst G obtained thereby contained 11.5% by weight of Ni and 5.8% by weight of tin (according to elemental analysis), corresponding to a Sn/Ni molar ratio of 0.25.

EXAMPLE 7 (Invention)

Preparation of a Catalyst H Supported on Silica and Containing Nickel and Tin Such that the Sn/Ni Molar Ratio=0.022

Another catalyst based on nickel and tin in accordance with the invention (catalyst H) was prepared from catalyst D using the following protocol. A quantity of 0.41 g of monometallic catalyst D was pre-reduced in a stream of hydrogen at 400° C. for 14 hours. The tin was deposited in the gas phase: 6.5 mg of tetrabutyltin (Aldrich) was injected at ambient temperature and in an atmosphere of hydrogen onto the pre-reduced catalyst D. After 3 hours of contact, the temperature was raised to 450° C. in a stream of hydrogen at a rate of 2° C./minute. The temperature was then maintained at 450° C. for 4 hours. Finally, the catalyst was cooled and stored in air.

Catalyst H obtained thereby contained 11.6% by weight of Ni and 0.5% by weight of tin (according to elemental analysis), corresponding to a Sn/Ni molar ratio of 0.022.

EXAMPLE 8

Catalytic Performances of Catalysts A to H in Styrene Hydrogenation

The catalytic properties of the catalysts prepared in the above examples were evaluated successively in a styrene hydrogenation process. The selective hydrogenation of styrene produces ethylbenzene, this hydrogenation constituting the desired reaction. The total hydrogenation of styrene produces ethylcyclohexane, which is produced by an unwanted, successive reaction.

Styrene was hydrogenated in a 100 mL stainless steel autoclave provided with mechanical, magnetically actuated stirring and which could function at a maximum pressure of 100 bar and at temperatures in the range 5° C. to 200° C.

Prior to its introduction into the autoclave, a quantity of 20 mg of catalyst was reduced in a stream of hydrogen at 400° C. for 14 hours then transferred into the autoclave in the absence of air. After adding 50 mL of n-heptane (Acros), the autoclave was sealed, purged then pressurized to 30 bar (0.3 MPa) of hydrogen and heated to the initial temperature of the test (40° C.). At time t=0, 3.5 g of styrene (Aldrich) and an internal reference were introduced into the autoclave and stirring was commenced (500 rpm). The progress of the reaction was monitored by taking samples from the reaction medium at regular time intervals. These samples were analyzed by gas chromatography. Once all of the styrene had been consumed, the autoclave was heated rapidly to 130° C. (in less than 1 hour): in this second step, the reaction that took place was the hydrogenation of ethylbenzene to ethylcyclohexane.

The reaction rates for the two reactions of hydrogenation of styrene to ethylbenzene and hydrogenation of ethylbenzene to ethylcyclohexane were defined as the slopes at the origin with respect to the mass of catalyst in the graphs of the change of ethylbenzene concentration with time. The reaction rate r1 for the hydrogenation of styrene to ethylbenzene was determined in the first step of the test. The reaction rate r2 for the hydrogenation of ethylbenzene to ethylcyclohexane was determined in the second step of the test. The selectivity of the catalyst for the desired product, namely ethylbenzene, was evaluated by the ratio r1/r2; the higher the ratio, the more selective is the catalyst for ethylbenzene.

In Tables 1 and 2, the reaction rates for the hydrogenation of styrene and the selectivities of the catalysts prepared in accordance with the above examples are compared with monometallic Ni catalysts.

TABLE 1

Styrene hydrogenation reaction rates and selectivities for catalysts supported on alumina. Comparison with monometallic catalyst A based on nickel alone

| Catalyst | Sn/Ni molar ratio | Styrene hydrogenation reaction rate (r1)/(r1$_{ref}$) | Selectivity (r1/r2)/(r1$_{ref}$/r2$_{ref}$) |
|---|---|---|---|
| A | 0 | 1 | 1 |
| B | 0.030 | 1.8 | 3.2 |
| C | 0.030 | 0.8 | 1.5 |

TABLE 2

Styrene hydrogenation reaction rates and selectivities for catalysts supported on silica. Comparison with monometallic catalyst D based on nickel alone

| Catalyst | Sn/Ni molar ratio | Styrene hydrogenation reaction rate (r1)/(r1$_{ref}$) | Selectivity (r1/r2)/(r1$_{ref}$/r2$_{ref}$) |
|---|---|---|---|
| D | 0 | 1 | 1 |
| E | 0.034 | 2.0 | 3.0 |
| F | 0.034 | 2.0 | 3.5 |
| G | 0.25 | 0.6 | 0.8 |
| H | 0.022 | 1.2 | 1.3 |

In Tables 1 and 2, r1$_{ref}$ and r2$_{ref}$ respectively correspond to the reaction rate r1 defined above, or respectively r2 defined above, measured using the corresponding monometallic catalyst.

Catalysts B, E and F based on nickel and tin, prepared in accordance with the process of the invention and with a Sn/Ni molar ratio of the order of 0.03, have satisfactory styrene to ethylbenzene hydrogenation rates which were a little higher than those for the corresponding nickel monometallic catalysts (catalysts A and D), which means that the performance as regards hydrogenation of the double bond present in the C2 group carried by the aromatic ring of the styrene was maintained or even improved. In particular, the selectivity of catalysts B, E and F was 3 to 4 times higher than that of the corresponding monometallic nickel catalysts (catalysts A and D). In addition, for catalysts B, E and F, hydrogenation of the aromatic ring was slowed compared with that observed with catalysts A and D, which favoured the production of ethylcyclohexane to the detriment of ethylbenzene. Thus, catalysts B, E and F are much more selective for ethylbenzene than catalysts A and D. Adding tin in a controlled quantity to a monometallic catalyst based on nickel can thus slow down the reaction for hydrogenation of the aromatic ring of styrene while retaining good double bond hydrogenation performance.

Catalyst G based on nickel and tin and with a Sn/Ni molar ratio of 0.25 showed that too much tin is deleterious both for the rate of hydrogenation of styrene to ethylbenzene and for the selectivity of the catalyst. Catalysts B, E and F, prepared in accordance with the process of the invention under conditions such that the Sn/Ni molar ratio of said catalysts is in the range 0.01 to 0.2, are much more selective towards ethylbenzene than catalyst G, which favoured the production of ethylcyclohexane to the detriment of ethylbenzene.

Catalyst H based on nickel and tin and with a Sn/Ni molar ratio of 0.022 shows that a small quantity of tin can increase the selectivity of the catalyst even though this increase is much smaller than that obtained with catalysts B, E or F.

Catalyst C based on nickel and tin, prepared in the liquid phase in the presence of an organic solvent (heptane) and with no activation step, also had a very low selectivity.

Catalysts B, E, F and H, prepared using the process of the invention and having a molar ratio in the range 0.01 to 2, thus result in substantially improved performances in terms of selectivity and the rate of hydrogenation of a double bond when they are used in a process for the selective hydrogenation of an alkenylaromatic compound such as styrene in the present case. Said catalysts B, E, F and H substantially promote hydrogenation of the double bond present in the C2 group carried by the aromatic ring of styrene to the detriment of hydrogenation of the benzene ring.

The preceding examples can be repeated with similar success by substituting the generically or specifically described reactants and/or operating conditions of this invention for those used in the preceding examples.

In the foregoing and in the examples and, all parts and percentages are by weight, unless otherwise indicated.

The entire disclosures of all applications, patents and publications, cited herein and of corresponding FR application Ser. No. 09/03.988, filed Aug. 17, 2009 are incorporated by reference herein.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. A process for preparing a catalyst comprising at least one porous support and at least one metallic phase containing nickel and tin in a proportion such that the Sn/Ni molar ratio is in the range of 0.01 to 0.2, said process comprising at least the following steps in succession:
 a) depositing nickel on at least said support in order to obtain a supported nickel-based monometallic catalyst;
 b) reducing said monometallic catalyst in the presence of at least one reducing gas;
 c) depositing, in the gas phase and in the presence of at least one reducing gas, at least one organometallic tin compound onto said reduced monometallic catalyst; and
 d) activating the solid derived from said step c) in the presence of at least one reducing gas in order to obtain a supported catalyst having a metallic phase based on nickel and tin in which the tin represents 0.02% to 15% by weight of the mass of said catalyst and the nickel represents 1% to 50% by weight of the mass of said catalyst with an Sn/Ni molar ratio in the range of 0.01 to 0.2.

2. A preparation process according to claim 1, in which said catalyst has a Sn/Ni molar ratio in the range of 0.025 to 0.055.

3. A preparation process according to claim 2, in which said catalyst has a Sn/Ni molar ratio in the range of 0.03 to 0.05.

4. A preparation process according to claim 1, in which said porous support present in said catalyst is an alumina or a silica.

5. A preparation process according to claim 1, in which said step b) is carried out at a temperature in the range of 100° C. to 600° C., for a period in the range 1 hour to 40 hours.

6. A preparation process according to claim 1, in which said step c) is carried out in the absence of solvent.

7. A preparation process according to claim 1, in which said organometallic compound employed in said step c) is of the formula $Sn(R)_n H_{4-n}$ where R is an alkyl radical or an aryl radical containing 1 to 12 carbon atoms and n is a whole number in the range of 1 to 4, radicals R being identical or different.

8. A preparation process according to claim 7, in which said organometallic tin compound is tetrabutyltin.

9. A preparation process according to claim 1, in which the reducing gas employed to carry out said step c) is hydrogen.

10. A preparation process according to claim 1, in which said step d) is carried out at a temperature in the range of 100° C. to 550° C. for a period in the range of 1 hour to 40 hours.

* * * * *